United States Patent [19]
Chatfield et al.

[11] Patent Number: 6,129,922
[45] Date of Patent: *Oct. 10, 2000

[54] METHODS FOR ADJUVANT FREE HEPATITIS A VIRUS VACCINATION

[75] Inventors: Steven Neville Chatfield, London; Mark Roberts, Glasgow, both of United Kingdom

[73] Assignee: Medeva Holdings B.V., ED Amsterdam, Netherlands

[ * ] Notice: This patent issued on a continued prosecution application filed under 37 CFR 1.53(d), and is subject to the twenty year patent term provisions of 35 U.S.C. 154(a)(2).

[21] Appl. No.: 08/596,318

[22] PCT Filed: Jun. 29, 1994

[86] PCT No.: PCT/GB94/01646

§ 371 Date: Feb. 8, 1996

§ 102(e) Date: Feb. 8, 1996

[87] PCT Pub. No.: WO95/05194

PCT Pub. Date: Feb. 23, 1995

[30] Foreign Application Priority Data

Aug. 12, 1993 [GB] United Kingdom ............. 9316745

[51] Int. Cl.[7] .................... A61K 39/29; C12Q 1/70
[52] U.S. Cl. ................... 424/226.1; 424/204.1; 435/69.1; 435/235.1; 435/320.1; 536/27.1; 536/23.72
[58] Field of Search ............. 435/235.1, 240.2, 435/320.1, 69.1; 536/27, 23.72; 424/226.1, 204.1

[56] References Cited

U.S. PATENT DOCUMENTS

| | | | |
|---|---|---|---|
| 5,294,548 | 3/1994 | McLinden et al. | 435/235.1 |
| 5,549,896 | 8/1996 | Gluck | 435/5 |
| 5,766,906 | 6/1998 | Lemon | 435/173.3 |

FOREIGN PATENT DOCUMENTS

| | | |
|---|---|---|
| 0418626 | 3/1991 | European Pat. Off. |
| 3135923 | 6/1991 | Japan. |
| WO93/01279 | 1/1993 | WIPO. |
| WO94/17827 | 8/1994 | WIPO. |

OTHER PUBLICATIONS

Lehner et al. Science 1992 vol. 258 (5086) p. 1365–1369.
Siogren et al., Vaccine 10 (Suppl. 1): S135–S137, 1992.
Hondt et al., Vaccine, vol. 10, Suppl. 1, S48–S52, 1992.
Karaviannis et al., J. Gen. Virol., 72: 2167–2172, 1991.
Johnston et al., J. Infectious Diseases, 157(6):1203–1211, Jun. 1988.

*Primary Examiner*—Ardin H. Marschel
*Assistant Examiner*—Mary K Zeman
*Attorney, Agent, or Firm*—Wolf, Greenfield & Sacks, P.C.

[57] ABSTRACT

The invention provides the use of Hepatitis A virus capsid, or a mucosally immunogenic fragment or epitope thereof, for the manufacture of a mucosal vaccine composition for administration to a mucosal surface of a patient to induce production of serum Immunoglobulin G antibody against Hepatitis A. Preferably the vaccine composition is administered by the intranasal route.

20 Claims, 1 Drawing Sheet

METHODS FOR ADJUVANT FREE HEPATITIS A VIRUS VACCINATION

RELATED APPLICATIONS

This application is a national stage application under 35 U.S.C. §371 of PCT/GB94/01646, filed Jun. 29, 1994. This application claims priority under 35 U.S.C. §119 to Great Britain application 9316745.0, filed Aug. 12, 1993.

The present invention relates to vaccine compositions for delivery to mucosal surfaces, and to a method of inducing, in a mammal, an immune response to an antigen by delivering the antigen to a mucosal surface of the mammal. More particularly, the present invention relates to vaccine compositions for inoculating a mammal such as a human against picornavirus infection and particularly Hepatitis A infection.

Hepatitis A is an acute disease caused by infection with a small picornavirus closely related to the poliovirus. Infection is spread by the faecal/oral route and consequently the disease in endemic in areas where hygiene and sanitation standards are low. The risk of travellers to developing countries acquiring Hepatitis A is far greater than that of contracting typhoid and cholera (40 and 800 times respectively).

The virus itself is not directly cytopathic. The liver damage resulting from Hepatitis A virus (HAV) infection arises from destruction of virally infected cells by the host's cytotoxic T-lymphocytes. There is only a single serotype of HAV and infection results in long-term immunity, characteristics that are ideal for developing Hepatitis A prophylaxis. Protection is mediated by neutralising antibodies that prevent entry of hepatitis A virus into hepatocytes. Passive immunisation with purified human serum γ-globulin provides short term protection against the disease and until recently this was the only means of preventing hepatitis A.

In recent years, HAV vaccines have been developed but development has focused on inactivated and live attenuated vaccines. Both types of vaccines are prepared from HAV propagated in tissue culture cells. HAV replication is slow and the majority of the virus remains cell associated, and consequently the viral yields are low and relatively commercially unattractive. The problem of low viral yield could be overcome by using recombinant techniques which allow for the production of large quantities of proteins. However, it is important to ensure correct processing and folding of HAV proteins because the known neutralising epitopes are conformationally dependent. It has proved difficult so far to obtain recombinant HAV antigens that elicit appropriate immune responses.

One recombinant HAV antigen that has proved successful in inducing protection against HAV when injected parenterally is the HAV capsid preparation developed by American Biogenetic Sciences. American Biogenetic Sciences have succeeded in producing empty HAV capsids in eucaryotic cells using vaccinia and baculovirus expression vectors. The recombinant capsids are recognised by neutralising monoclonal antibodies, induce protection against HAV in chimpanzees when injected parenterally and are produced in considerably larger quantities than that obtained by conventional means. The HAV capsids are disclosed in International Patent Application WO-A-9301279, the disclosure in which is incorporated herein by reference.

A disadvantage with many vaccination regimens is that it is frequently necessary to administer the vaccine composition by means of injection, a factor which has a potential deterrent effect to many people, particularly when follow-up or booster injections are required to complete a course of treatment. One way of overcoming this problem would be to administer the vaccine composition to the oral or nasal mucosa, but although immunisation by the oral or intranasal route has been explored with certain other antigens, it has been found usually to be less effective in evoking serum antibodies than parenteral immunisation. For example, the article by M. H. Sjogren et al, Vaccine, Vol. 10, Suppl. 1, S135–S137, 1992, describes the administration of a live attenuated hepatitis A vaccine by either the oral route or the intramuscular route. Whereas intramuscular administration elicited a good serum antibody response, an antibody response to oral administration was not observed at any dose.

The fact that there are very few mucosal vaccines commercially available indicates that there are problems with developing such vaccines. May non-living soluble antigens, particularly those used traditionally by immunologists, such as ovalbumin (OVA) and Keyhole Limpet Haemocyanin (KLH) are poor mucosal immunogens. Large doses of such antigens are necessary to induce any responses but large doses can also cause tolerance in the individual to subsequent parenteral exposure to antigen, a condition known as Oral Tolerance. Although some microbial components such as the cholera toxin (CT) or E.coli heat labile toxin (LT) or the non-toxic binding portions of these toxins (CT-B and LT-B) have been found to be potent mucosal immunogens eliciting strong secretory and circulating antibodies, the reasons why such molecules are good mucosal immunogens has not been fully elucidated. One property that may be important is the ability of these molecules to bind to mucosal epithelial cells via certain surface receptors, although it has been found in studies by others that there is not necessarily a correlation between the ability of an antigen to bind to eucaryotic cells and its mucosal immunogenicity. In the present case, it is not known, at the molecular or cellular level, how HAV enters the body, nor is it known whether specific receptors are involved.

Thus, as far as we are aware, there is currently no way of predicting with any certainty whether a given antigen will possess good mucosal immunogenicity.

It has now been found that the recombinant empty HAV capsid referred to hereinabove, when administered mucosally, and in particular intranasally, is efficient at inducing serum anti-HAV antibodies. Thus, when the HAV capsid preparation was administered intranasally, following first and second booster doses, seroconversion to anti-HAV was observed in the majority of animals, and this compared favourably with the administration of the antigen in the presence of an alum adjuvant by the subcutaneous route.

Accordingly, in a first aspect, the invention provides the use of Hepatitis A virus capsid, or mucosally immunogenic fragments or epitopes thereof, for the manufacture of a mucosal vaccine composition for administration to a mucosal surface of a patient to induce the production of serum Immunoglobulin G antibody against Hepatitis A virus.

In a second aspect, the invention provides a vaccine composition for application to a mucosal surface, the composition comprising Hepatitis A virus capsid, or a mucosally immunogenic fragment or epitope thereof, and a pharmaceutically acceptable carrier.

In a still further aspect of the invention, there is provided a method of inducing the production of serum Immunoglobulin G antibody against Hepatitis A virus in a host such as a mammal (eg. human), which method comprises administering an effective amount of a Hepatitis A virus capsid antigen, or a mucosally immunogenic fragment or epitope thereof, directly to a mucosal surface in the host.

The mucosal delivery compositions of the present invention can be formulated, for example, for delivery to one or more of the oral, gastro intestinal, and respiratory (eg. nasal and bronchial) mucosa.

Where the composition is intended for delivery to the respiratory (eg. nasal or bronchial) mucosa, typically it is formulated as an aqueous solution for administration as an aerosol or nasal drops, or as a dry powder eg. for inhalation.

Compositions for administration as nasal drops may contain one or more excipients of the type usually included in such compositions, for example, preservatives, viscosity adjusting agents, tonicity adjusting agents, buffering agents and the like. The vaccine compositions of the present invention may also take the form of compositions intended to deliver the antigen to mucosal surfaces in the gastro intestinal tract. Such compositions can be provided with means for preventing degradation of the antigens by the gastric juices, for example by encasing the vaccine preparation in a capsule within a protective matrix or coating of known type.

The quantity of Hepatitis virus A capsid administered to the patient typically is selected such that it is non-toxic to the patient at concentrations employed to elicit an immune response. For example, the concentration of capsid administered may lie in the range 0.1 mg to 100 mg per kg/host.

The invention will now be illustrated in more detail by reference to the specific embodiments described in the following examples, and illustrated in the accompanying drawings. The examples are intended to be purely illustrative of the invention and are not intended to limit its scope in any way.

Figure 1:
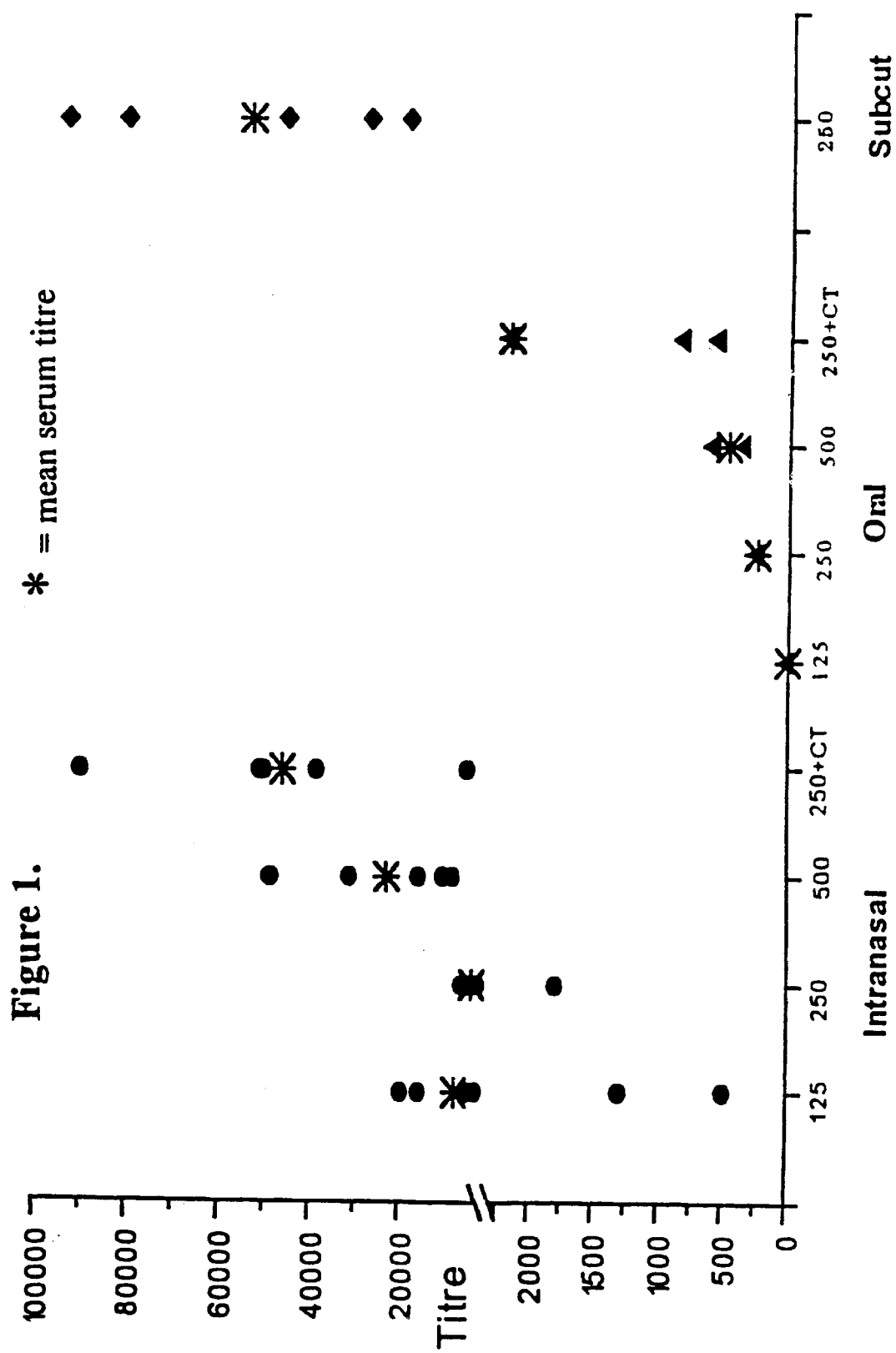
FIG. 1 illustrates the individual and mean serum anti-HAV titres following three doses of HAV capsids by each of the intranasal, oral and subcutaneous routes.

A sample of recombinant HAV capsids was obtained from American Biogenetic Sciences, Reyniers Germ Free Building, P.O. Box 1001 Notre Dame, Ind. 46556, USA. The sample was prepared from vaccinia-HAV infected Vero cells. Cells were lysed with NP40 and then extracted with trichlorotrifluroethane. The aqueous phase was concentrated and then chromatofocussed on Biogel A-15 column. Fractions containing empty capsids were pooled and concentrated. Formalin was added to inactivate any remaining vaccinia virus. The content of HAV capsids in the sample as given below is expressed in terms of ELISA units (EU). The EU values have been standardised on a sample of Hepatitis A virus obtained from SmithKline Beecham. The sample received contained 52 ELISA units (EU) HAV capsids per µl. The protein content of the sample was 30 mg/ml of which 100 ng/ml was estimated to be HAV antigen.

Recombinant HAV capsids of the aforementioned type can be prepared in accordance with the methods as set out in International Patent Application WO-A-9301279 (PCT/US92/05714).

Mice were immunised orally and intranasally (I/N) with different doses of HAV. A small quantity (1 µgm) of cholera toxin (CT) was included in the material given to some groups of mice to act as an adjuvant. CT was used because it is the most potent mucosal adjuvant known. A separate group of mice were immunised parenterally with HAV adsorbed to aluminium hydroxide as an adjuvant as a positive control. The groups were as set out in Table 1 below:

TABLE 1

| Group | Number of Mice | Dose Elisa Units (EU) | Adjuvants |
|---|---|---|---|
| 1. Parenteral | 5 | 250 × 3 | Alum |
| 2. Parenteral Control | 5 | — | Alum |
| 3. Oral | 10 | 500 × 3 | — |
| 4. Oral | 10 | 250 × 3 | — |
| 5. Oral | 10 | 125 × 3 | — |
| 6. Oral | 10 | 250 × 3 | CT[a] |
| 7. Oral Control | 5 | — | CT |
| 8. I/N[b] | 10 | | — |
| 9. I/N | 10 | 500 × 3 | — |
| 10. I/N | 10 | 250 × 3 | — |
| 11. I/N | 10 | 125 × 3 | CT |
| 12. I/N Control | 5 | 250 × 3 | CT |

[a]CT, Cholerae toxin (1 µg/dose)
[b]I/N, intranasal

| Day | Procedure |
|---|---|
| 0 | Primary immunisation |
| 20 | Sample bleed |
| 24 | 1st booster immunisation |
| 31 | Bleed, gut and nasal washes |
| 47 | 2nd booster immunisation |
| 54 | Sample bleed |

The immunisation was carried out by the method set out in Table 2 below:

TABLE 2

IMMUNISATION DETAILS

| Route | Volume Delivered (µl) | Diluent | Apparatus | Anaesthetic (Halothane) |
|---|---|---|---|---|
| Intranasal | 30 | PBS | micro pipette | light |
| Oral | 200 | 5% Bicarbonate sol. | gavage needle | light |
| Subcutaneous | 100 | PBS | needle | nil |

Anti-HAV responses were analysed using a capture ELISA technique as follows. Human convalescent polyclonal serum from an individual with known Hepatitis A was coated on 96 well plastic plates. The polyclonal serum captures HAV capsids binding them to the plate. Mouse serum was then incubated with the HAV capsid bound plates and the mouse serum reactivity to HAV determined using labelled anti-mouse antibodies. The protocol for the assay was as follows:

PROTOCOL (All volumes 50 µL/well unless otherwise stated)

1) Coat Costar EIA plates (Cat no: 3590) overnight, 4° C., with 1:25000 human capture antibody diluted in PBS.
2) Wash plate ×3 with phosphate buffered saline/Tween (0.05%) (PBST).
3) Block 1 hr, 37° C., 1%BSA(Sigma, Cat no: A7888) in PBST(200 µl/well).

4) Wash plate ×3 PBST.
5) Coat plates with sample containing HAV (0.1 EU/µl) in PBST (0.1%BSA), 2–3 hours 37° C.
6) Wash plate ×3 PBST.
7) Incubate plate with mouse serum diluted PBST, 2–3 hours, 37° C.
8) Wash plate ×3 PBST.
9) Incubate, 1–2 hours, 37° C., with anti-mouse IgG, 1:1000 (goat, Sigma, Cat No: B7022) in PBST.
10) Wash plate ×3 PBST.
11) Incubate, 1–2 hours, 37° C., with Streptavidin-peroxidase 1:1000 (Dako, Cat No: P397) in PBST.
12) Wash plate ×3 PBST.
13) Add substrate, OPD in phosphate-citrate buffer (Sigma, Cat no: P8287), incubate for up to 30 mins 37° C.
14) Read colour development after stopping substrate reaction (3MH$_2$SO$_4$).
Human sera and HAV capsid sample supplied by ABS. Optimum conditions of capture Antibody and HAV capsid sample were selected to minimise the S/N ratio.
Problems of high background noise, attributed to reactivity of the mouse serum against the human sera capture antibody were encountered. Reduction of the background was obtained by diluting out the capture antibody, beyond the dilution recommended by ABS.
Similar results for capsid capture were obtained using, 1:1000–1:25000 dilutions of the capture Antibody.
The serum IgG anti-HAV responses were as shown in Table 3 below:

TABLE 3

Mean serum IgG anti-HAV response following a primary and booster immunisations

| | Titre | | | | | | | | Sub/cut |
|---|---|---|---|---|---|---|---|---|---|
| | Intranasal | | | | Oral | | | | |
| Dose | 125 | 250 | 500 | 250 + CT | 125 | 250 | 500 | 250 + CT | 250 + Alum |
| 1 | <50 | <50 | 50 | 6000 | <50 | <50 | <50 | <50 | 6000 |
| 2 | <250 | 250 | 9462 | 8772 | <250 | <250 | <250 | <250 | 10438 |
| 3 | 7650 | 3777 | 23030 | 46250 | <250 | 250 | 480 | 2170 | 54000 |

Mean titre calculated from responding mice only

As can be seen from the Table, after a single dose, anti-HAV antibodies could be detected in the sera of mice immunised subcutaneously with 250 EU and intranasally with 500 EU. There was no detectable response in any of the other groups. Boosting greatly enhanced the response in the subcutaneous and intranasal 500 groups, giving titres of approximately 10500 and 9500 respectively. Also, a very similar response was seen in mice receiving 250 EU plus CT I/N and a low but measurable response was detected in the sera of half the mice receiving two doses of 250 EU I/N. No serum response was detectable in any of the orally immunised mice at this point. Further boosting did result in seroconversion of some of the orally immunised mice into 250 EU, 500 EU and 250 EU+CT groups. The response was greatest in the later group. After three doses, all of the I/N immunised mice had seroconverted, the magnitude of the response being dose dependant in the absence of CT. I/N immunisation with 500 EU, 250 EU+CT produced high serum titres that were slightly lower but comparable to those produced by S/C immunisation with 250 EU, HAV adsorbed to alum.

FIG. 1 illustrates the individual and mean serum anti-HAV titres following three doses of HAV capsids. As can be seen, CT greatly augmented the serum anti-HAV response of I/N and orally administered antigen. The titres in mice receiving 250 EU+CT I/N were more than 10-fold rated at each time point than those evoked by I/N immunisation with 250 EU alone. There was a similar difference in anti-HAV titre in the mice immunised orally with 250 EU with and without CT. CT also increased the number of mice seroconverting. Moreover, the titres in the I/N 250 EU+CT group follow each immunisation were very similar to those of mice given 250 EU adsorbed to alum and given subcutaneously.

Table 2 below shows the number of mice in the different groups seroconverting following the first and second booster doses. Seroconversion was dose and route dependant. Subcutaneous immunisation with 2 doses of 250 EU led to seroconversion in all the mice, whereas the same dose, only half of the mice to whom the antigen had been administered intranasally, and none of the mice to whom antigen had been administered orally, had seroconverted. After the second boost, all of the mice in the I/N groups had seroconverted, including those in the 125 EU dose group that exhibited no response after two doses. Likewise, the orally immunised mice started a response after the second boost although even the addition of CT did not result in the seroconversion of all of the mice.

TABLE 4

Rate of seroconversion to anti-HAV following the first and second booster immunisations

| | Intranasal | | | | Oral | | | | Sub/cut |
|---|---|---|---|---|---|---|---|---|---|
| Dose | 125 | 250 | 500 | 250 + CT | 125 | 250 | 500 CT | 250 + | 250 + Alum |
| 2 | 0/4* | 2/4 | 4/4 | 4/4 | 0/4 | 0/4 | 0/4 | 0/4 | 5/5 |
| 3 | 6/6 | 5/5 | 5/5 | 5/5 | 0/4 | 1/4 | 2/4 | 3/4 | 5/5 |

*No. of mice responding/No. of mice tested

Table 4 shows the number of mice in the different groups seroconverting following the first and second booster doses. Seroconversion was dose and route dependant. subcutaneous immunisations with two doses of 250 EU led to seroconversion in all the mice, whereas at the same dose only half of the mice treated intranasally and none of the mice treated orally had seroconverted. After the second boost all of the mice in the intranasal groups had seroconverted, including those in the 125 EU dose group that exhibited no response after 2 doses. Likewise the orally immunised mice started to respond after the second boost although even the addition of CT did not result in the seroconversion of all of the mice.

The aforementioned examples are given by way of illustration only and are not intended the scope of the application, which is limited only by the claims appended hereto.

What is claimed is:

1. A method of inducing the production of serum Immunoglobulin G antibody against Hepatitis A virus in a host, which method comprises administering, in an amount effective for inducing the production of serum Immunoglobulin G antibody against Hepatitis A virus, Hepatitis A virus capsid antigens to a mucosal surface in the host, wherein the Hepatitis A virus capsid antigens are formulated without adjuvant.

2. The method of claim 1 wherein the Hepatitis A virus capsid antigens are recombinantly produced.

3. The method of claim 1 wherein the Hepatitis A virus capsid antigens are administered to the nasal mucosa.

4. The method of claim 1 wherein the Hepatitis A virus capsid antigens are administered to the oral mucosa.

5. The method of claim 1 wherein the Hepatitis A virus capsid antigens are formulated as an aqueous solution for administration as an aerosol or nasal drops.

6. The method of claim 1 wherein the Hepatitis A virus capsid antigens are formulated as a dry powder for inhalation.

7. The method of claim 1 wherein the host is a mammal.

8. A method of inducing the production of serum Immunoglobulin G antibody against Hepatitis A virus in a host, which method comprises administering intranasally, in an amount effective for inducing the production of serum Immunoglobulin G antibody against Hepatitis A virus, Hepatitis A virus capsid antigens to a mucosal surface in the host, wherein the Hepatitis A virus capsid antigens are formulated without adjuvant.

9. The method of claim 8 wherein the Hepatitis A virus capsid antigens are recombinantly produced.

10. The method of claim 8 wherein the Hepatitis A virus capsid antigens are formulated as an aqueous solution for administration as an aerosol or nasal drops.

11. The method of claim 8 wherein the Hepatitis A virus capsid antigens are formulated as a dry powder for inhalation.

12. The method of claim 8 wherein the host is a mammal.

13. A method of inducing the production of serum Immunoglobulin G antibody against Hepatitis A virus in a host, which method comprises administering intranasally, in an amount effective for inducing the production of serum Immunoglobulin G antibody against Hepatitis A virus, Hepatitis A virus capsids to a mucosal surface in the host, wherein the Hepatitis A virus capsids are formulated without adjuvant.

14. The method of claim 13 wherein the Hepatitis A virus capsids are recombinantly produced.

15. The method of claim 13 wherein the Hepatitis A virus capsids are formulated as an aqueous solution for administration as an aerosol or nasal drops.

16. The method of claim 13 wherein the Hepatitis A virus capsids are formulated as a dry powder for inhalation.

17. The method of claim 13 wherein the host is a mammal.

18. A method of inducing the production of serum Immunoglobulin G antibody against Hepatitis A virus in a host, which method comprises administering, in an amount effective for inducing the production of serum Immunoglobulin G antibody against Hepatitis A virus, a Hepatitis A virus antigen in capsid form to a mucosal surface in the host, wherein the Hepatitis A virus capsid antigen is formulated without adjuvant.

19. The method of claim 18 wherein the Hepatitis A virus antigen is recombinantly produced.

20. The method of claim 18 wherein the Hepatitis A virus capsid antigen is administered to the nasal mucosa.

* * * * *